United States Patent
McIntyre

(10) Patent No.: US 8,226,672 B2
(45) Date of Patent: *Jul. 24, 2012

(54) DEVICE AND METHOD FOR TEMPORARY VESSEL OCCLUSION

(75) Inventor: Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 318 days.

This patent is subject to a terminal disclaimer.

(21) Appl. No.: 12/684,414

(22) Filed: Jan. 8, 2010

(65) Prior Publication Data

US 2010/0114134 A1    May 6, 2010

Related U.S. Application Data

(63) Continuation of application No. 11/416,349, filed on May 1, 2006, now Pat. No. 7,666,199.

(51) Int. Cl.
*A61B 17/06* (2006.01)

(52) U.S. Cl. ............................................. 606/158
(58) Field of Classification Search .................. 606/158, 606/232, 144; 128/830, 31, 898, 833
See application file for complete search history.

(56) References Cited

U.S. PATENT DOCUMENTS 3,409,014 A * 11/1968 Shannon ........................ 606/148
6,099,553 A *  8/2000 Hart et al. ..................... 606/232

* cited by examiner

*Primary Examiner* — Corrine M McDermott
*Assistant Examiner* — Christina Lauer
(74) *Attorney, Agent, or Firm* — Fay Kaplun & Marcin, LLP

(57) ABSTRACT

A method of occluding a vessel, comprises forming an incision through tissue covering the vessel to expose a portion of the vessel and looping a first suture around the vessel such that ends of the first suture extend out of the incision in combination with closing the incision with the ends of the first suture protruding through the closed incision, placing a force distribution element over the incision and tightening the first suture over the force distribution element to form a kink in the vessel.

16 Claims, 2 Drawing Sheets

DEVICE AND METHOD FOR TEMPORARY VESSEL OCCLUSION

PRIORITY CLAIM

The present application is a Continuation of U.S. patent application Ser. No. 11/416,349 filed on May 1, 2006, now U.S. Pat. No. 7,666,199, the entire disclosure of this patent is expressly incorporated herein by reference.

BACKGROUND

A variety of medical procedures involve temporary restriction or stoppage of blood flow to a target region to, for example, prevent excessive bleeding during a procedure or to necrose the target tissue. This is often done by occluding the artery or arteries supplying the target region.

Uterine fibroids have been treated by occluding the supply of blood thereto. However, complex surgical procedures may be required to occlude the targeted vessels, adding to the expense and time required for the treatment. It may also be difficult to achieve a desired degree of occlusion without damaging the targeted vessel(s) or the surrounding tissue. Many current methods are also irreversible or reversible only through complicated and/or painful procedures.

SUMMARY OF THE INVENTION

In one aspect, the present invention is directed to a method of occluding a vessel, comprising forming an incision through tissue covering the vessel to expose a portion of the vessel and looping a first suture around the vessel such that ends of the first suture extend out of the incision in combination with closing the incision with the ends of the first suture protruding through the closed incision, placing a force distribution element over the incision and tightening the first suture over the force distribution element to form a kink in the vessel.

DETAILED DESCRIPTION

Figure 1:
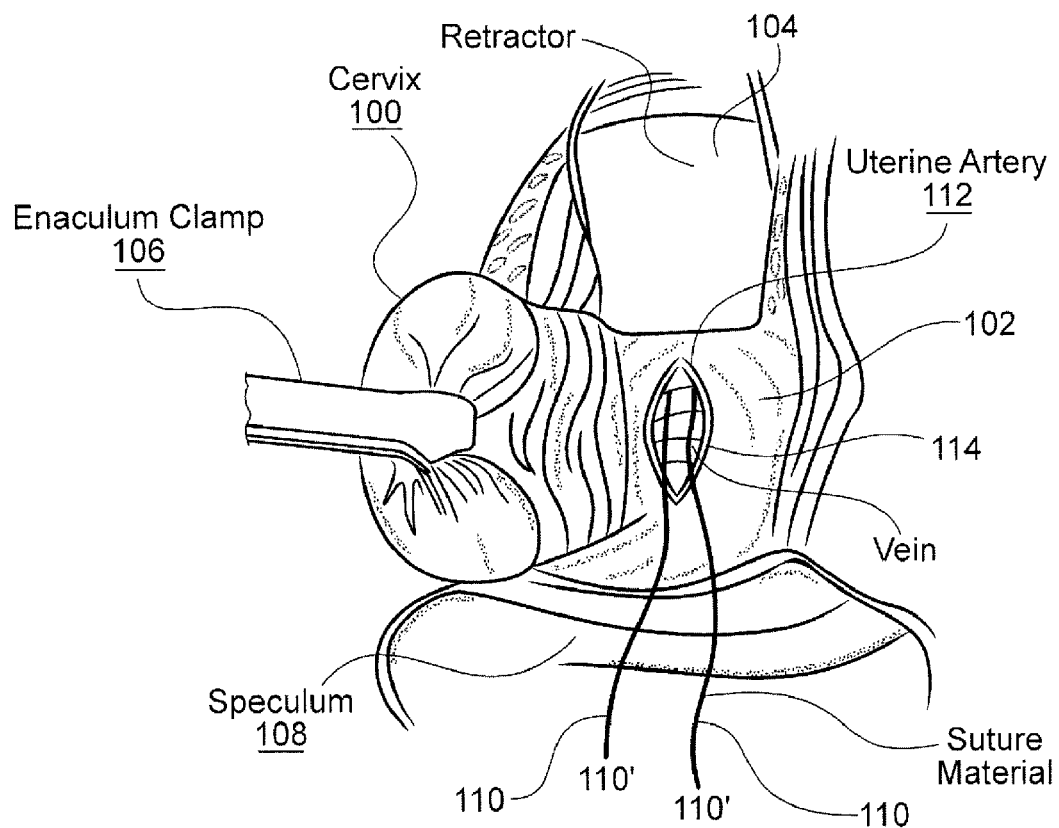
FIG. 1 is a diagram showing an initial step of a blood vessel occlusion procedure according to the invention.

The present invention may be further understood with reference to the following description and to the appended drawings, wherein like elements are referred to with the same reference numerals. As described above, the present invention relates to devices and methods for reducing or stopping blood flow to target tissue. In particular, the present invention relates to devices and methods for occluding uterine arteries, for example, to treat fibroids.

The method and device according to the invention facilitates access to one or more target blood vessels to better ensure that blood flow to the target tissue is reduced to a desired degree or stopped, if desired. Furthermore, the procedure is reversible and injury to the surrounding tissue is minimized as forces applied to those tissues by the occluding sutures are distributed over a larger area.

A procedure according to embodiments of the present invention, generally comprises exposing target blood vessels (e.g., target uterine arteries) by incising the vaginal fornix and constricting each of the target arteries (e.g., by tightening a loop of suture therearound) to kink each target artery and cut-off blood flow therethrough. A specially shaped force distribution member is used to spread the force of each suture or other loop over a wide area of the overlying tissue to prevent damage as the suture is tightened therearound. Without the force distribution member the suture may cut through the tissue over time. The force distribution member also provides a platform that gives access to intentionally cut the suture against at such time as the physician wishes to remove the force distribution member and the sutures.

As shown in FIG. 1, an exemplary procedure involves making two incisions 114 in the vaginal fornix 102 at locations defined approximately by the 3 and 9 o'clock positions as one faces the cervix 100. Each of the incisions exposes one of the uterine arteries 112, so that the surgeon is able to manipulate the uterine artery 112 as needed. As would be understood by those skilled in the art, a tenaculum clamp 106 may be used to manipulate the cervix 100 and a conventional retractor 104 and speculum 108 may be used to facilitate positioning the tissue and making the incision 114 by exposing the sides of the vaginal fornix 102.

Once the uterine artery 112 has been exposed, the surgeon forms a loop around the target blood vessel with a suture 110 or other similar material so that both ends 110' of the suture 110 extend out of the incision 114. In this configuration, the suture 110 enters the incision 114, loops around the artery 112 and then exits the incision 114. The suture 110 is cut to a length that leaves a substantial amount of material hanging outside of the incision 114, so that the two ends 110' can be manipulated to form one or more knots, as necessary to carry out the steps according to the invention. The suture 110 is trimmed so that the length thereof is sufficient to permit the inclusion of additional devices behind the knots, as will be described in greater detail below.

Figure 2:
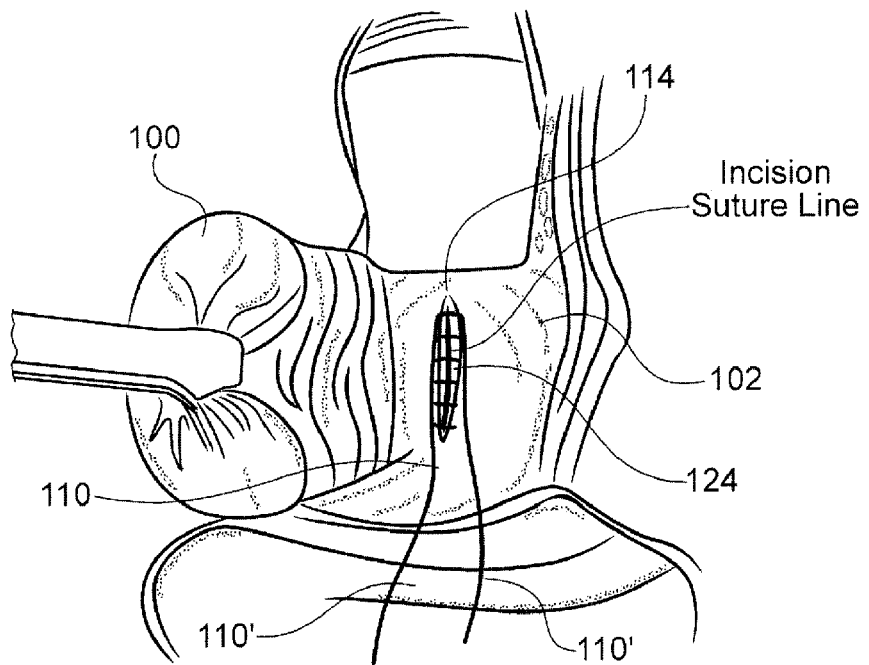
FIG. 2 is a diagram showing a second step of the blood vessel occlusion according to the invention.

After the suture 110 is in position around the target uterine artery 112, the incision 114 is closed, e.g., using a second suture 124, as shown in FIG. 2. The ends 110' of the suture 110 are left to extend beyond the closed incision 114 through the suture 124, so that they may be manipulated while a portion of the suture 110 remains looped around the artery 112, within the now closed incision 114. This condition is shown clearly in FIG. 2, and is repeated for both uterine arteries being treated.

In a different embodiment, the suture 110 may be replaced with a different material or device that can be looped around the artery 112 to extend out through the incision 114. For example, a strip of mesh material or another ribbon-like material may be used instead of a conventional filament-like suture to achieve the same result. The material used may also vary depending on the application. For example, the material for the suture or ribbon may be permanent or bio-absorbable, such as PGA, PDO, poliglecaprone, polydioxanone, panacryl or caprosyn. The use of bio-absorbable material simplifies the procedure as there is no need to remove the suture 110 after its purpose has been accomplished. The flow of blood will be restored as the suture is absorbed into the body.

Figure 3:
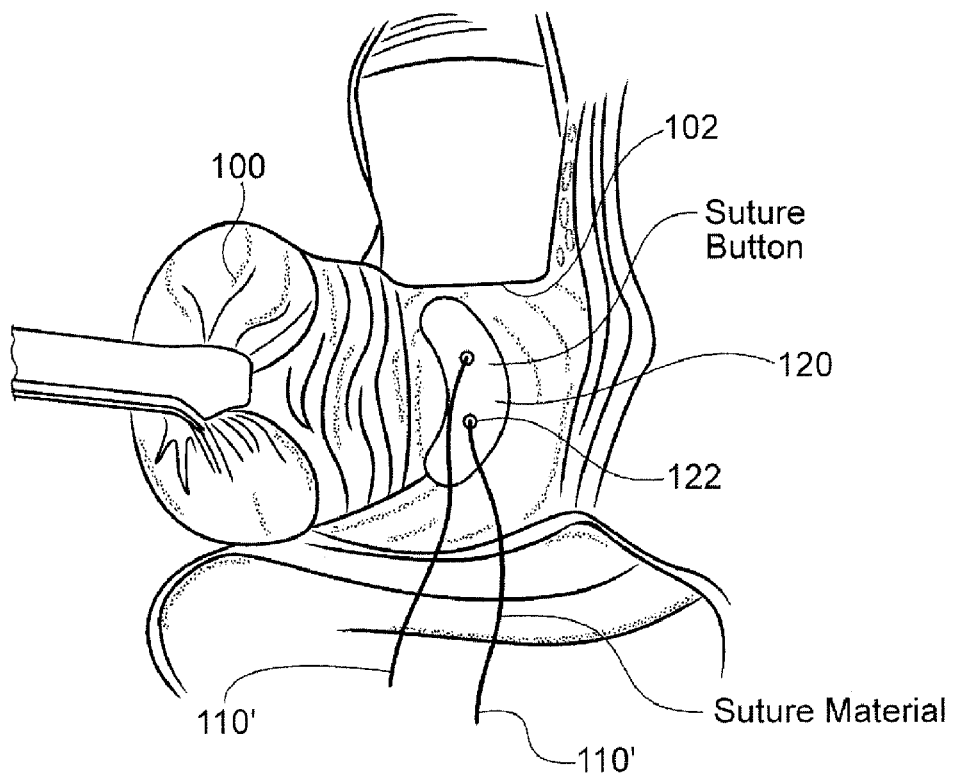
FIG. 3 is a diagram showing a step using a suture button of the blood vessel occlusion according to the invention.
Figure 4:
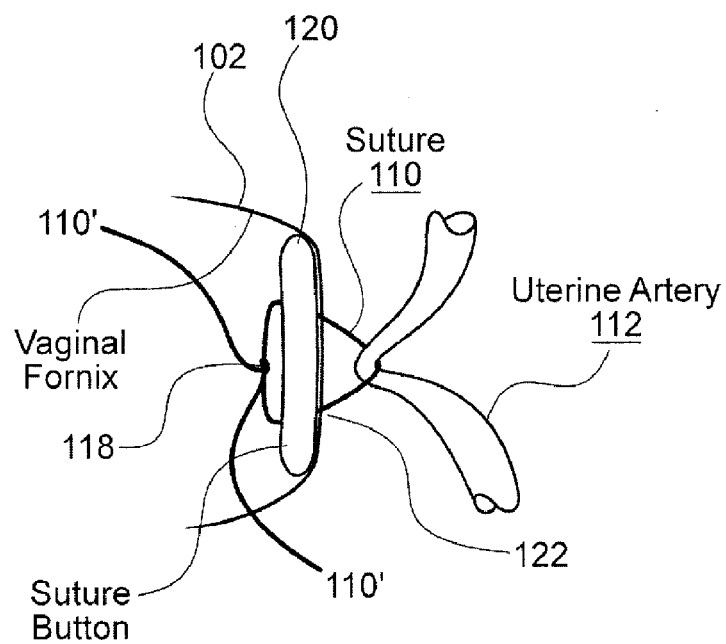
FIG. 4 is a side elevation view showing the suture button used in the blood vessel occlusion accordance with the present invention.

As shown in FIG. 4, after the second suture 124 has been closed, the loop of suture 110 is tightened around the uterine artery 112 to kink and occlude it. As shown in FIGS. 3 and 4, this embodiment of the present invention also includes a force distribution element to prevent the thin material of the suture 110 from cutting into the tissue of the vaginal fornix 102. The force distribution element spreads the compressive force from the suture 110 over a larger portion of the surface of the vaginal fornix. More specifically, in this embodiment a button 120 is applied over the second suture 124 to overlie the incision 114 and form a barrier between the tissue of the vaginal fornix 102 and the tightening suture 110.

A first face of the button 120 preferably has a shape closely matching a curvature of the vaginal fornix 102, so that substantially all of the first face contacts the tissue of the fornix 102. The peripheral outline of the button 120 is also selected to fit comfortably within the vaginal fornix 102 against the cervix without causing pressure points. For example, the button 120 is preferably generally kidney-shaped. Alternatively, the button 120 may take any other shape that allows it to cover the incision 114 and the second suture line 124, without causing undue discomfort. The material forming the button 120 may be either permanent or bio-absorbable. For example, polyethylene, polypropylene, polycarbonate, nylon, teflon and ABS may be used to construct the button 120.

Furthermore, the button 120 is preferably formed of a low friction material to reduce resistance to the passing of the suture 110 through the orifices 122. This facilitates tying and tightening the knot or knots 118. In embodiments that utilize bio-absorbable materials to form the button 120 and the sutures 110, no follow up procedure is required to remove these elements. Thus, the required hospitalization time and the overall cost of the procedure may be reduced. As would be understood by those skilled in the art, the composition of the suture 110 and of the button 120 are preferably selected to control the amount of time that the target artery is occluded to achieve a desired therapeutic result.

The exemplary button 120 comprises two openings 122 that allow the two ends 110' of the suture 110 to pass though, from the first face facing the fornix 102 to the opposite side of the button 120. Those skilled in the art will understand that the openings 122 may be either holes as shown or notches in an outer edge of the button 120. The suture 110 is drawn through the button 120 to press the button up against the fornix 102 and to kink and occlude the artery 112. Then a knot 118 is tied with the ends 110' to maintain the compressive force around the artery 112. Additional knots may be tied with the ends 110' and pushed down over the original knot 118 to reinforce the position of the button 120 and prevent loosening of the pressure applied around the uterine artery 112.

The steps described above may then be repeated on the other side of the cervix 102, to occlude the second uterine artery 112. As described above, two incisions are made on opposite sides of the vaginal fornix 102, to provide access to both uterine arteries 112 that have to be occluded to successfully treat uterine fibroids.

After the button 120 has been tightened in place with the knot or knots 118, it is left in place for a desired period of time. For example, depending on the reason for the occlusion and the desired effect on the target tissue, the occlusion may be kept in place for 24 hours or less. At the end of the period, if bio-absorbable materials are not used, the surgeon cuts the suture 110 and removes both the button 120 and the suture 110 from the incision 114. The procedure is repeated on both uterine arteries 112 to restore normal blood flow therethrough and thus to the uterus. In a typical procedure the process necroses the uterine fibroids and causing them to shrink over the subsequent 3-6 months. This reduces symptoms such as discomfort from the bulk of the fibroids and abnormal bleeding.

Although the description of the embodiments of the invention presented above is directed primarily to a procedure to occlude uterine arteries and to cause the necrosis of uterine fibroids, those skilled in the art will recognize that the method and apparatus according to the invention may be used in any application where it is desired to reduce or completely stop fluid flow through a vessel or vessels.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A method of occluding a vessel, comprising:
   forming an incision through tissue covering the vessel to expose a portion of the vessel;
   looping a material around the vessel such that ends of the material extend out of the incision;
   closing the incision with the ends of the material protruding through the closed incision;
   placing a force distribution element over the incision; and
   tightening the material over the force distribution element to form a kink in the vessel.

2. The method according to claim 1, further comprising:
   closing the incision with a second material.

3. The method according to claim 1, further comprising:
   threading the ends of the material through openings in the force distribution element.

4. The method according to claim 3, wherein a first one of the openings comprises a hole through the force distribution element.

5. The method according to claim 3, wherein a first one of the openings comprises a notch formed in an edge of the force distribution element.

6. The method according to claim 1, wherein a tissue contacting surface of the force distribution member is contoured to match a shape of the tissue.

7. The method according to claim 1, wherein the vessel is a first uterine artery and the tissue is a vaginal fornix.

8. The method according to claim 7, further comprising:
   repeating steps of forming the incision, looping the material, placing the force distribution element and tightening the material for a second uterine artery.

9. The method according to claim 7, wherein the force distribution element is placed between the cervix and the vaginal fornix.

10. The method according to claim 7, further comprising:
    using at least one of a tenaculum clamp, a speculum and a retractor to prepare the vaginal fornix.

11. The method according to claim 1, wherein the force distribution element is formed of one of polyethylene, polypropylene, polycarbonate, nylon, ABS and teflon.

12. The method according to claim 1, wherein the force distribution element is made of a bio-absorbable material.

13. The method according to claim 1, wherein the material is formed of a bio-absorbable material.

14. The method according to claim 1, further comprising:
    removing the force distribution element and the material after a selected period of time.

15. The method according to claim 1, wherein the material includes one of a suture, a ribbon, and a strip of mesh.

16. The method according to claim 1, wherein the material is made of one of PGA, PDO, poliglecaprone, polydioxanone, panacryl, and caprosyn.

* * * * *